United States Patent
Blumhofer

(10) Patent No.: US 10,388,013 B2
(45) Date of Patent: Aug. 20, 2019

(54) MATCHING PATIENT IMAGES AND IMAGES OF AN ANATOMICAL ATLAS

(71) Applicant: Brainlab AG, Munich (DE)

(72) Inventor: Andreas Blumhofer, Neubiberg (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/608,485

(22) Filed: May 30, 2017

(65) Prior Publication Data

US 2017/0330324 A1    Nov. 16, 2017

Related U.S. Application Data

(62) Division of application No. 14/438,436, filed as application No. PCT/EP2012/071241 on Oct. 26, 2012, now Pat. No. 9,704,243.

(51) Int. Cl.
*G06K 9/00* (2006.01)
*G06T 7/00* (2017.01)
(Continued)

(52) U.S. Cl.
CPC .......... *G06T 7/0012* (2013.01); *G06T 3/0056* (2013.01); *G06T 7/30* (2017.01);
(Continued)

(58) Field of Classification Search
None
See application file for complete search history.

(56) References Cited

U.S. PATENT DOCUMENTS 6,611,630 B1    8/2003  Miller et al.
6,740,883 B1    5/2004  Stodilka et al.
(Continued)

FOREIGN PATENT DOCUMENTS

CN    102262699    9/2012
EP    1239921      9/2002
(Continued)

OTHER PUBLICATIONS

Christensen et al., "Synthesizing Average 3D Anatomical Shapes" NeuroImage, vol. 32, Aug. 2006, pp. 146-158.
(Continued)

*Primary Examiner* — Shervin K Nakhjavan
(74) *Attorney, Agent, or Firm* — Tucker Ellis LLP

(57) ABSTRACT

A matching transformation is determined for matching a patient image set of images of an anatomical body structure of a patient with an atlas image set of images of a general anatomical structure including anatomical atlas elements. Atlas spatial information containing spatial information on the general anatomical structure, and element representation information are obtained. The element representation information describes representation data sets which contain information on representations of the plurality of atlas elements in the atlas images to be determined are obtained, and also describes a determination rule for determining respective representation data sets for respective atlas elements in accordance with different respective parameter sets. Patient data is acquired by acquiring the patient image set and the parameter sets which are respectively associated with the images of the patient image set. The matching transformation is determined by matching images associated with the same parameter set to each other.

18 Claims, 6 Drawing Sheets

(51) Int. Cl.
*G16H 30/40* (2018.01)
*G06T 7/30* (2017.01)
*G06T 7/32* (2017.01)
*G06T 7/38* (2017.01)
*G06T 11/00* (2006.01)
*G06T 3/00* (2006.01)
*G16H 50/50* (2018.01)

(52) U.S. Cl.
CPC ............... *G06T 7/32* (2017.01); *G06T 7/38* (2017.01); *G06T 11/008* (2013.01); *G16H 30/40* (2018.01); *G06T 2207/10004* (2013.01); *G06T 2207/10076* (2013.01); *G06T 2207/10081* (2013.01); *G06T 2207/10084* (2013.01); *G06T 2207/10088* (2013.01); *G06T 2207/10116* (2013.01); *G06T 2207/20081* (2013.01); *G06T 2207/20104* (2013.01); *G06T 2207/20128* (2013.01); *G06T 2207/20221* (2013.01); *G06T 2207/30004* (2013.01); *G06T 2207/30196* (2013.01); *G16H 50/50* (2018.01)

(56) References Cited

U.S. PATENT DOCUMENTS

| | | | |
|---|---|---|---|
| 6,754,374 B1 | 6/2004 | Miller | |
| 7,167,583 B1* | 1/2007 | Lipson | G06K 9/00 361/720 |
| 7,324,842 B2* | 1/2008 | Dale | A61B 5/055 382/128 |
| 8,577,115 B2 | 11/2013 | Gering | |
| 8,666,128 B2* | 3/2014 | Chaney | G06K 9/621 382/128 |
| 8,804,619 B2 | 8/2014 | Sorensen et al. | |
| 8,805,619 B2* | 8/2014 | Sorensen | A61B 5/055 702/19 |
| 9,406,130 B2 | 8/2016 | Vilsmeier | |
| 2001/0036302 A1 | 11/2001 | Miller | |
| 2003/0011624 A1 | 1/2003 | Ellis | |
| 2003/0013951 A1* | 1/2003 | Stefanescu | G06F 17/30256 600/407 |
| 2003/0228042 A1 | 12/2003 | Sinha | |
| 2005/0101855 A1 | 5/2005 | Miga | |
| 2005/0182319 A1 | 8/2005 | Glossop | |
| 2006/0004274 A1 | 1/2006 | Hawman | |
| 2006/0058641 A1* | 3/2006 | Krieg | A61B 5/055 600/416 |
| 2006/0239519 A1* | 10/2006 | Nowinski | G06K 9/3233 382/128 |
| 2007/0019846 A1 | 1/2007 | Bullitt et al. | |
| 2007/0038058 A1 | 2/2007 | West et al. | |
| 2008/0080788 A1 | 4/2008 | Nord et al. | |
| 2008/0123927 A1* | 5/2008 | Miga | G06F 19/00 382/131 |
| 2008/0186311 A1* | 8/2008 | Claus | A61B 6/032 345/420 |
| 2008/0188741 A1 | 8/2008 | Mallya | |
| 2009/0024181 A1 | 1/2009 | Raghavan | |
| 2009/0060308 A1 | 3/2009 | Dawant et al. | |
| 2009/0087124 A1* | 4/2009 | Nord | A61N 5/1049 382/296 |
| 2009/0220136 A1* | 9/2009 | Bova | A61B 6/5247 382/131 |
| 2009/0226060 A1* | 9/2009 | Gering | G06T 7/11 382/128 |
| 2009/0228299 A1* | 9/2009 | Kangarloo | G06F 19/321 705/2 |
| 2009/0287271 A1 | 11/2009 | Blum et al. | |
| 2010/0002921 A1* | 1/2010 | Fenchel | A61B 5/055 382/128 |
| 2010/0119127 A1 | 5/2010 | Bello et al. | |
| 2010/0179428 A1 | 7/2010 | Pedersen et al. | |
| 2010/0286995 A1* | 11/2010 | Pekar | G06Q 50/22 705/2 |
| 2011/0019885 A1* | 1/2011 | Bond | G06F 19/321 382/128 |
| 2011/0069873 A1 | 3/2011 | Azemoto et al. | |
| 2011/0085716 A1 | 4/2011 | Chefd'hotel | |
| 2011/0160543 A1 | 6/2011 | Parsey | |
| 2011/0194739 A1* | 8/2011 | Vincent | G06K 9/6209 382/128 |
| 2011/0216954 A1* | 9/2011 | Sundar | G06T 7/0024 382/131 |
| 2011/0235884 A1* | 9/2011 | Schreibmann | A61B 6/037 382/131 |
| 2012/0027278 A1 | 2/2012 | Chaney | |
| 2012/0143090 A1 | 6/2012 | Hay et al. | |
| 2012/0155734 A1* | 6/2012 | Barratt | G06T 7/344 382/131 |
| 2012/0163687 A1* | 6/2012 | Plakas | G06T 7/0038 382/131 |
| 2012/0265271 A1 | 10/2012 | Goetz | |
| 2012/0281900 A1 | 11/2012 | Rueckert et al. | |
| 2012/0314924 A1 | 12/2012 | Carlton | |
| 2013/0034203 A1* | 2/2013 | Wang | A61B 6/03 378/41 |
| 2013/0044927 A1* | 2/2013 | Poole | G06T 7/0014 382/131 |
| 2013/0063434 A1 | 3/2013 | Miga | |
| 2013/0070978 A1 | 3/2013 | Hyde et al. | |
| 2013/0116749 A1 | 5/2013 | Carlton et al. | |
| 2013/0172727 A1 | 7/2013 | Mori et al. | |
| 2014/0358114 A1* | 12/2014 | Rosenbluth | G06F 19/00 604/500 |
| 2015/0254838 A1 | 9/2015 | Blumhofer | |
| 2015/0278471 A1 | 10/2015 | Blumhofer | |
| 2015/0287195 A1 | 10/2015 | Vilsmeier | |
| 2015/0287198 A1* | 10/2015 | Vilsmeier | G06T 7/0014 382/128 |
| 2015/0294467 A1 | 10/2015 | Blumhofer | |
| 2016/0232655 A1 | 8/2016 | Lancher | |

FOREIGN PATENT DOCUMENTS

| | | |
|---|---|---|
| EP | 1814453 | 8/2007 |
| EP | 1868157 | 12/2007 |
| EP | 1890261 | 7/2008 |
| EP | 2131212 | 12/2009 |
| WO | 2008041125 | 4/2008 |
| WO | 2014063840 | 5/2014 |
| WO | 2014063840 A1 | 5/2015 |

OTHER PUBLICATIONS

Gousias et al., Automatic Segmentation of Pediatric Brain MRIs using a Maximum Probability Pediatric Atlas, Imaging Systems and Techniques, 2012 IEEE International Conference, Jul. 2012, pp. 251-265.

Ehrhardt et al., "Statistical Modeling of 4D Respiratory Lung Motion Using Diffeomorphic Image Registration" IEEE Transactions on Medical Imaging, vol. 30. No. 2, Feb. 2011, pp. 251-265.

Guimond et al., "Average Brain Models: A Convergence Study", Computer Vision and Image Understanding vol. 77, Issue 2, Feb. 2000, pp. 192-210.

International Search Report and Written Opinion for International Application No. PCT/EP2012/071241 dated May 3, 2013, pp. 1-6.

Dumpuri et al., "Automated brain shift correction using a pre-computed deformation atlas", Proceedings of SPIE, vol. 6141, Mar. 2, 2006, pp. 61411F-1-61411F-8, XP055291281, DOI: 10.117/12.652350, ISBN: 978-1-5106-1533-5 US.

Kmelinskii et al., "Articulated Whole-body Atlases for Small Animal Image Analysis: Construction and Applications", Molecular Imaging and Biology, Springer-Verlag, NE vol. 13. No. 5, Sep. 8, 2010, pp. 898-910, XP019956310, ISSN: 1860-2002, DOI: 10.1007/511307-010-0386-X.

Backhaus et al.,"The Cardiac Atlas Project: Towards a Map of the Heart" In: "Patient-Specific Modeling of the Cardiovascular System", 2010, Springer New York, New York, NY, XP055519296, ISBN: 978-1-4419-669, 1-9 pages 113-129, DOI: 10.1007/978-1-4419-6691-9_7.

(56) References Cited

OTHER PUBLICATIONS

International Search Report and Written Opinion for PCT/EP2013/063640, dated Oct. 18, 2013, 9 pages.
International Search Report and Written Opinion for PCT/EP2013/072009 dated Mar. 7, 2014, 10 pages.
Zacharaki et al., "Orbit: A Multiresolution Framework for Deformable Registration of Brain Tumor Images", IEEE Transactions of Medical Imaging, vol. 27 No. 8, Aug. 2008, pp. 1003-1017.
Zacharaki et al., "Non-diffeomorphic registration of brain tumor images by simulating tissue loss and tumor growth", NeuroImage 46, Feb. 5, 2009, pp. 762-774.
Bach Cuadra et al., "Atlas-Based Segmentation of Pathological MR Brain Images Using a Model of Lesion Growth", IEEE Transactions on Medical Imaging, vol. 23 No. 10, Oct. 2004, pp. 1301-1314.
Prastawa et al., "Simulation of brain tumors in MR images for evaluation of segmentation efficiency", Medical Image Analysis 13, Dec. 3, 2008, pp. 297-311.
Zacharaki et al., "A comparative study of biomechanical simulators in deformable registration of brain tumor Images" NIH-PA Author Manuscript, Department of Radiology, University of Pennsylvania, Philadelphia, PA 19104 U.S.A., IEEE Trans Biomed Eng. Mar. 2008; 55 (3): 1233-1236. doi:10.1109/TBME.2007.905484, 10 pages.
Clatz et al., "In silico tumor growth: application to glioblastomas" In proceeding of: Medical Image Computing and Computer-Assisted Intervention—MICCAI 2004, pp. 337-345, Sep. 26-29, 2004, Proceedings, Part II, 7th. International Conference, Saint-Malo, France).
Zacharaki et al., "Parallel optimization of tumor model parameters for fast registration of brain tumor images" Department of Mechanical Engineering and Applied Mechanics, University of Pennsylvania, Philadelphia PA. U.S.A., Medical Imaging 2008: Image Processing, edited by Joseph M. Reinhardt, Josien P.W. Pluim, Proc. of SPIE vol. 6914, 69140K, (2008) 1605-7422/08/$18 doi: 10.1117/12.767788, 10 pages.
De Craene et al., "Dense Deformation Field Estimation of Atlas-based Segmentation of Pathological MR Brain Images" Article in Computer Methods and Programs in Biomedicine 84 (2006) pp. 66-75, Elsevier Ireland Ltd.
Stefanescu et al., "Non-Rigid Atlas to Subject Registration with Pathologies for Conformal Brain Radiotherapy", Medical Image Computing and Computer-Assisted Intervention-MICCAI 2004, Lecture notes in Computer Science vol. 3216, 2004, pp. 704-711, Saint Malo, France, (Preprint) 9 pages.
Dawant et al., "Brain Atlas Deformation in Presence of Large Space-Occupying Tumors" Department of Electrical and Computer Engineering and Department of Biomedical Engineering, Vanderbilt University, Nashville, Tennessee U.S.A., Medical Image Computing and Computer-Assisted Intervention—MICCAI, 1999, vol. 1679, pp. 589-596.
D'Haese et al., "Atlas-based segmentation of the brain for 3-dimensional treatment planning in children with Infratentorial ependymoma", Medical Image Computing and Computer-Assisted Intervention—MICCAI 2003 Proceedings, Lecture notes in Computer Science vol. 2879 pp. 627-634.
Clatz et al.,"Realistic Simulation of the 3D Growth of Brain Tumors in MR Images Coupling Diffusion with Biomechanical Deformation", NIH-PA Author Manscript, IEEE trans Med Imaging, Oct. 2005; 24 (10):1334-1346, doi: 10.1109/TMI.2005.857217, pp. 1-36.
Miller et al.,"Biomechanics of the brain for computer-integrated surgery" Intelligent Systems for Medicine Laboratory, School of Mechanical Engineering, The University of Western Australia, Acta of Bioengineering and Biomechanics, vol. 12, No. 2, 2010, pp. 25-37.
Hogea et al.,"Fast Solvers for Soft Tissue Simulation with Application to Construction of Brain Tumor Atlases" pp. 1-16, Biomedical Image Analysis, Department of Radiology, University of Pennsylvania, Philadelphia, PA U.S.A., Published 2007.
Shirinifard et al., "3D Multi-Cell Simulation of Tumor Growth and Angiogenesis", PLoS ONE 4, e7190, pp. 1-11 (2009).

Moghaddasi et al., "In Silico Modelling of Tumour Margin Diffusion and Infiltration: Review of Current Status", Computational and Mathematical Methods in Medicine, Article ID 672895, 16 pages (2012).
Alarcon et al., "A cellular automaton model for tumour growth in inhomogeneous environment", Journal of Theoretical Biology 225, pp. 257-274 (2003).
Angelini et al., "Glioma Dynamics and Computational Models: A Review of Segmentation, Registration, and In Silico Growth Algorithms and their Clinical Applications", Current Medical Imaging Reviews 3, pp. 262-276 (2007).
Kansal et al., "Simulated Brain Tumor Growth Dynamics Using a Three-Dimensional Cellular Automaton", J. theor. Biol. 2003, pp. 367-382 (2000).
Karantasis et al., "Accelerating the simulation of brain tumor proliferation with many-core GPUs", Journal of Computational Science 3, pp. 306-313 (2012).
Volkau et al. "Indirect interpolation of subcortical structures in the Talairach-Tournoux atlas" Medical Imaging 2004; Visualization, Image-Guided Procedures, and Display, edited by Robert L Galloway, Jr., Proceedings of SPIE vol. 5367 (SPIE, Bellingham, WA, 2004) pp. 533-537.
Nenzhe et al. "Cardiac Image Super-Resolution with Global Correspondence Using Multi-Atlas PatchMatch" K. Mori at al. (Eds.) MICCAI 2013, Part III, LNCS 8151, pp. 9-16, 2013 © Springer-Verlag Berlin Heidelberg 2013.
Chintalapani et al."Statistical Atlas Based Extrapolation of CT Data" Medical Imaging 2010: Visualization, Image-Guided Procedures, and Modeling, edited by Kenneth H. Wong, Michael I. Miga, Proc. of SPIE vol. 7625, 762539-© 2010 SPIE, pp. 1-10.
Lamecker et al."Atlas-based 3D-Shape Reconstruction from X-Ray Images" Proceedings of the 18th International conference on Pattern Recognition (ICPR'06) 0-7695-2521-0/06 ©2006 IEEE, pp. 1-4.
Dowling et al."An Atlas-Based Electron Density Mapping Method for Magnetic Resonance Imaging (MRI)—Alone Treatment Planning and Adaptive MRI-Based Prostate Radiation Therapy" Int J Radiation Oncol Biol Phys, vol. 83 No. 1, pp. e5-11, 2012 ©2012 Elsevier Inc.
International Search Report for PCT/EP2013/070331; dated Mar. 17, 2014; p. 1-3, EPO, NL-2280.
European Patent Office, International Preliminary Report on Patentability for corresponding PCT/2013/070331, dated Apr. 5, 2016. p. 1-10.
Herman et al., "Shape-based Interpolation", Article, IEEE Computer Graphics and Applications, IEEE Service Center, New York, NY, US, vol. 12 No. 3, May 1992, pp. 69-79, XP011417304, ISSN: 0272-1716, DOI: 10.1109/38.135915.
H.Greenspan, "Super-Resolution in Medical Imaging", Article, The Computer Journal, vol. 52, No. 1, 2008, pp. 43-63, XP055055156, ISSN:0010-4620, DOI: 10.1093/comjnl/bxm075.
European Patent Office, EP Examiner Hermann Borotschnig, Office Action, "Consultation by telephone with the applicant" dated Feb. 21, 2017 for parallel EP patent Application No: 13774107.0, dated Mar. 9, 2017, pp. 1-18.
Christensen, et al., "Synthesizing average 3D anatomical shapes", Neuroimage, Academic Press, Orlando, FL, US. vol. 32, No. 1, Aug. 1, 2006, pp. 146-158, XP024906133.
Ioannis, et al., "Automatic Segmentation of pediatric brain MRIs using a maximum probability pediatric atlas", Imaging Systems and techniques (1st), 2012 IEEE International Conference On, IEEE, Jul. 16, 2012, pp. 95-100, XP032237216.
Ehrhardt, et al., "Statistical Modeling of 4D Respiratory Lung Motion Using Diffeomorphic Image Registration", IEEE Transactions on Medical Imaging, IEEE Service Center, Piscataway, NJ, US vol. 30, No. 2, Feb. 1, 2011 pp. 251-265, XP011330316.
Suimond, et al.,"Average Brain Models: A Convergence Study", Computer Vision and Image Understanding, Academic press, US, vol. 77, No. 2, Feb. 1, 2000, pp. 192-210, XP004439302.
European Patent Office, International Search Report for PCT/EP2013/072005, dated Jul. 24, 2014, pp. 1-3.
Züich, K.J.Brain Tumors (Springer Berlin Heidelberg, 1986). Excerpt of pp. 128-132.

(56) References Cited

OTHER PUBLICATIONS

Andersen, S.M., Rapcsak, S.Z & Beeson, P.M. Cost function masking during normalization of brains with focal lesions: Still a necessity? Neuroimage 53, 78-84 (2010) (7 pages).
Züich, K.J Tumor and Brain. Chapter 10 of Brain Tumors, pp. 154-182 (Springer Berlin Heidelberg, 1986).
Gousias et al., "Automatic Segmentation of Pediatric Brain MRIs using a Maximum Probability Pediatric Atlas", IEEE 2012, 6 pages.
Joshi el al ("DigiWarp: a method for deformable mouse atlas warping to surface topographic data", phys, Med, Biol, 2010)(Year: 2010).
Notice of Allowance for related U.S. Appl. No. 15/608,578, dated Apr. 19, 2019.

* cited by examiner

Table 3

| representation data set | representation information (visual appearance) |
|---|---|
| a | |
| b | |
| c | |
| ⋮ | |
| g | |
| h | |
| i | |

S123 acquiring a description of representation data sets

S124 acquiring the determination rule by performing the steps of:

- selecting a representation class on the basis of an atlas element identifier, using Table 1;

- determining a representation data set on the basis of the selected representation class and the parameter set associated with the patient image, using Table 2;

- determining the representation of the atlas element on the basis of the determined representation data set, using Table 3.

Figure 1B

MATCHING PATIENT IMAGES AND IMAGES OF AN ANATOMICAL ATLAS

RELATED APPLICATION DATA

This application is a divisional of U.S. patent application Ser. No. 14/438,436 filed Apr. 24, 2015, which is the U.S. National Stage of International Application No. PCT/EP2012/071241 filed Oct. 26, 2012, the entire contents of each of which are incorporated herein by reference.

BACKGROUND

The present invention is directed to determining a transformation (a matching transformation) which (in particular non-rigidly) matches a set of one or more images of an anatomical body structure of a human or animal patient and a set of one or more images of a general anatomical structure of a patient model as described by an anatomical atlas, by matching respective images of the sets to each other, in particular using image fusion, wherein the respective images are associated with the same parameter set (see below) and represent one or more anatomical elements which are matched to each other and correspond to each other.

The anatomical atlas (or "atlas" for short) describes the general anatomical structure of the complete body of a patient model or an object in the patient model or in particular a plurality of objects in the patient model which in particular have a defined positional relationship with respect to each other. An object can comprise one or more anatomical elements. The atlas can be a two-dimensional or three-dimensional (static) atlas or a time-dependent two-dimensional or three-dimensional atlas (a so-called 4D atlas).

SUMMARY

The object of the invention is to enable the matching transformation to be determined.

This object is achieved by the subject matter of the independent claims. The dependent claims are directed to advantageous embodiments of the invention.

A data processing method is advantageously provided for determining the matching transformation. The matching transformation matches a set of one or more images of an anatomical body structure of a patient and a set of one or more images of a general anatomical structure. The set of one or more images of the anatomical body structure of the patient is referred to as the patient image set. The anatomical body structure comprises anatomical elements as sub-structures. The set of one or more images of the general anatomical structure is referred to as the atlas image set. As described below, the atlas image set is determined (in particular generated) in accordance with patient data including one or more parameter sets and on the basis of atlas data. Determining the atlas image set is thus flexible and can be adapted to the particular situation presented by the patient data. The particular situation presented by the patient data is in particular defined by the anatomical elements represented in the patient images, which are referred to as the patient elements, and by at least one parameter set which is associated with the patient image set. A parameter set represents and in particular comprises parameters which have an influence on (generating) an image ("patient image") of an anatomical body structure (by means of an analytical device). In particular, the parameters have an influence on the representation, in particular the visual appearance, of the anatomical body structure (in particular the anatomical elements) in the (patient) image. The parameters are therefore also referred to as "representation parameters". The parameter set represents and in particular comprises parameters which describe the type of an analytical device and in particular measurement parameters of the analytical device. One example of a representation parameter is a particular image modality used for generating the patient image set. One particular example of a representation parameter is a DICOM (Digital Imaging and Communications in Medicine). The patient image set can of course also or instead comprise patient images associated with other representation parameters, in particular different image modalities such as computer tomography (CT) and magnetic resonance (MR). The image modalities are in particular further specified by means of measurement parameters used for adjusting the analytical device, such as the voltage or magnetic field strength. The measurement parameters are also an example of representation parameters. There may be many different parameters involved when generating an analytical image of an anatomical structure by means of an analytical device, all of which constitute examples of representation parameters. The representation of patient elements in patient images can for example depend on the magnetic field strengths used during MR, the repetition time, the echo time, the inversion time, the flip angle, etc.

In the field of medicine, imaging methods (imaging modalities) are used to generate image data (for example, two-dimensional or three-dimensional image data) of anatomical structures (such as soft tissues, bones, organs, etc.) of the human body. The term "medical imaging methods" is understood to refer to imaging methods, advantageously apparatus-based imaging methods (so-called medical imaging modalities, in particular radiological imaging methods), such as for instance computer tomography (CT) and cone beam computer tomography (CBCT; in particular, volumetric CBCT), x-ray tomography, magnetic resonance tomography (MRT or MRI=magnetic resonance imaging), in particular $T_1$-weighted MRI, $T_2$-weighted MRI, PET (with and without contrast agent), conventional x-ray, sonography and/or ultrasound examinations. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body.

In order to determine the geometry and/or position of an anatomical body structure, analytical devices such as x-ray devices, CT devices or MRT devices are used to generate analytical images (such as x-ray images or MRT images) of the anatomical body structure. Analytical devices in particular use imaging methods and are in particular devices for analysing a patient's body, for instance by using waves and/or radiation and/or energy beams, in particular electromagnetic waves and/or radiation, ultrasound waves and/or particle beams. Analytical devices are in particular devices which generate images (for example, two-dimensional or three-dimensional images) of the patient's body (in particular, the anatomical body structure of the patient's body) by analysing the body. Analytical devices are in particular used in medical diagnosis, in particular in radiology.

The above-mentioned parameter sets represent and in particular comprise one or in particular more (representation) parameters (such as the type of analytical device and magnetic field strength in MRT devices or the voltage in CT devices) which reflect (and in particular are) parameters which have an influence on the representation of the patient elements in the patient image, in particular when generating the patient image. Thus, each of the patient images is associated with a particular parameter set. Different patient images can be and in particular are associated with different parameter sets. The parameters which the parameter sets comprise in particular represent parameters which have an influence on the representation of the patient elements in the patient images when the images are generated. Examples of influences on representation include influences on the image values which represent the anatomical elements (such as for instance influences on a grey value which represents the anatomical element or influences on the position of an image value in a colour space which represents the anatomical element). Other examples include influences on contrast, image value range, gamut, etc.

The method in accordance with the invention in particular comprises the step of acquiring atlas data which contain information describing the general anatomical structure and in particular the representation of the general anatomical structure in an analytical image. This information is referred to as "element representation information". The element representation information describes the representation of the anatomical elements (referred to as "atlas elements") of the general anatomical structure. This representation corresponds to the representation of the anatomical elements in an image which is generated by means of an analytical device from a patient having an anatomical structure which is identical to the general anatomical structure. The influence of the generating process (for example, scanning parameters such as the type of analytical device used to generate the image and/or the measurement parameters which are set, in particular adjusted, on the analytical device and have an influence on the representation) on the representation of the one or more anatomical elements is represented by the parameter set. The atlas data, in particular a determination rule (see below) in combination with the parameter set, allow the atlas image to be determined.

The method also comprises the step of acquiring the patient data which include the patient image set and one or more of the parameter sets. Preferably, only one of the one or more parameter sets is respectively associated with one of the one or more patient images of the patient image set.

The general anatomical structure can be the anatomical structure of a complete body or the anatomical structure of only a part of the body. The general anatomical structure preferably comprises a plurality of atlas elements. The atlas elements which the general anatomical structure comprises are preferably not assigned a particular representation data set. The representation data sets can for instance describe a grey value of an atlas element. Since the atlas elements of the general anatomical structure are preferably not assigned a particular grey value, these atlas elements are also referred to here as "white atlas elements".

The anatomical structure described by the patient images can be a description of the anatomical structure of the complete body or a description of the anatomical structure of only a part of the body. The term "part" as used here can encompass either the term "complete" or the term "less than complete", i.e. only partial (within the common meaning of this term). Data (referred to as "correspondence part data") are preferably acquired which describe the part of the general anatomical structure which corresponds to the anatomical structure represented by the patient images and which is to be matched. If the entire general anatomical structure described by the atlas data is to be matched, then correspondence part data are not necessary. The (different) patient images of the patient image set preferably each describe at least approximately the same part of the anatomical structure of a patient's body. The (different) patient images of the patient image set preferably cover the description of at least one particular part of the body, i.e. at least one particular part of the body is reflected in all of the patient images of the patient image set, which is then referred to as the "common part" and comprises common anatomical elements. The matching transformation is preferably determined for at least the part of the patient images which reflect the common part of the body. The correspondence part data can comprise data (referred to as "correspondence element data") which describe the white atlas elements for which a matching transformation is to be determined. The white atlas elements for which the matching transformation is to be determined are referred to as "corresponding elements" and can be acquired for instance by receiving indication information (from a user) which indicates which white atlas elements are corresponding elements. Alternatively or additionally, the correspondence part data can be determined for example by performing a rigid transformation which rigidly matches patient images and atlas images which are respectively associated with the same parameter set, in particular without deforming the atlas elements represented in the atlas image and without deforming the patient image. Merely scaling and/or rotating the atlas images and patient images in order to achieve rigid matching is not considered to constitute deformation. In order to perform rigid matching, atlas spatial information (referred to as "coarse atlas spatial information") is preferably used which describes the general anatomical structure in less detail than the atlas spatial information used for determining the atlas images, in order to reduce the data processing load. Additionally or alternatively, the correspondence part data can describe the part (referred to as the "atlas part") of the general anatomical structure (the complete structure or only a particular part of it) which is to be used for the matching transformation and in particular can describe the part of the anatomical structure (referred to as the "patient part") represented in the at least one patient image (i.e. all of the anatomical structure or only a part of it) which is to be used for the matching transformation. At least one preliminary atlas image is then generated which represents the atlas part. Preliminary rigid matching is then performed, without deforming the atlas elements, in which the at least one preliminary atlas image and the patient part of the anatomical structure represented in the at least one patient image are matched to each other. Rigid matching in particular allows a common reference system to be established for all of the atlas images determined. The common reference system is in particular used to determine the matching transformation. This common reference system facilitates the implementation of "coupled deformation" as described below.

The data processing method of the present invention in particular comprises the above-mentioned step of determining the correspondence part data, in particular the corresponding elements. The term "corresponding" as used here means in particular "anatomically the same", in particular "representing the same anatomical part" which can be understood to be a part of a patient's body which is present in a plurality of different patient's bodies and in particular belongs to the same representation classes (see below for the definition of representation classes) and/or consists of the same material and/or is located at least approximately at the same location relative to other anatomical elements and/or has a similar geometry (size and/or shape) in a plurality of different patients.

The atlas data preferably comprise atlas spatial information which spatially describes the general anatomical structure and in particular the white atlas elements. The spatial information can comprise only one set of static spatial information, i.e. spatial information which does not change over time and only provides one set of spatial properties for the general anatomical structure, or can comprise a plurality of sets of static spatial information which respectively describe the spatial properties of the general anatomical structure in different states, for instance at different points in time during for example a vital movement such as for example the breathing cycle. In particular, the spatial information describes the spatial properties, i.e. the relative position, of white atlas elements within the general anatomical structure with respect to each other and/or the geometry (size and/or shape) of the atlas elements and is preferably used to determine the spatial properties (i.e. the position and/or geometry) of the atlas elements represented in the atlas images.

A vital movement is a movement of parts of the body due to vital functions of the body, such as for example breathing and/or the heart beat. The term "vital movement" covers any kind of movement of the body which is performed unconsciously and in particular controlled by the brain stem.

The above-mentioned plurality of sets of spatial properties of the general anatomical structure can also describe different movement or posture states of the patient, such as the patient running, walking, standing or lying down. It can also cover different pathological states of a patient, such as a patient with an infection or tumour(s) in particular parts of the body, or particular states of a patient during surgery, such as a patient with an exposed skull resulting in a brain shift (which can in turn depend on the positioning of the head). The term "posture" as used here refers in particular to different positions of the extremities of the body, such as for example with the hands raised or lowered.

The element representation information describes a plurality of representation data sets, wherein "plurality" as used here means a discrete number of representation data sets (as for example described by a table) or a continuous multitude of representation data sets (as for example described by a function). Preferably, both the atlas spatial information and the element representation information are used to determine the atlas images. The representation data sets contain information describing representations of the plurality of atlas elements in the atlas images which are to be determined. In particular, the element representation information comprises information on the visual appearance of the atlas element (in an atlas image) and in particular does not include the above-mentioned spatial information. The representation information describes for example an image value (for instance, a grey value) for the respective atlas elements.

The same patient elements can be represented differently in different patient images, depending on the parameter sets. Correspondingly, the element representation information preferably does not comprise just one representation data set to be determined for respective white atlas elements but rather a plurality of representation data sets to be determined for respective white atlas elements, wherein each of the plurality of representation data sets (for each of the white atlas elements) is in particular respectively associated with one of the plurality of parameter sets. A white atlas element to which a representation data set is assigned is referred to here as a "grey atlas element", i.e. a plurality of different grey atlas elements can be determined on the basis of the white atlas elements and a plurality of different representation data sets. It is possible, on the basis of the element representation information, to determine the grey atlas elements (i.e. the representation and in particular visual appearance of a corresponding element) in an atlas image in accordance with the parameter set of a patient image which is to be matched to the atlas image. In other words, the grey atlas elements in an atlas image are determined on the basis of the parameter set of the patient image.

The patient data consist of the patient image set, i.e. one or more patient images associated with one or more parameter sets, and a description of the one or more associated parameter sets. The parameter sets associated with the patient data are preferably identical to one or more of the plurality of parameter sets of the atlas data for which the determination rule describes a determination of the representation data sets, in order to allow for a straightforward application of the determination rule. If such identity does not obtain, then the parameter set of the atlas data which is most similar to the parameter set of the patient data is preferably selected, in order to be able to apply the determination rule.

As mentioned above, the one or more atlas images are determined on the basis of the atlas data and the patient data. The one or more atlas images respectively represent at least a part of the general anatomical structure (i.e. the complete general anatomical structure or only a part of it). The respectively determined one or more atlas images represent a part of the general anatomical structure in accordance with the part of the spatial information which relates to said part of the general anatomical structure. In other words, the spatial information on the general anatomical structure, in particular the part of the spatial information which relates to atlas elements represented in the set of atlas images, is used to determine the set of atlas images. In order to determine the representation of the general anatomical structure in the set of atlas images, the representation data sets which are part of the description of the atlas data are specifically used. The determination rule described by the atlas data is applied in order to determine the representation data sets which are specifically to be used to determine the representation of the atlas elements. The determination rule refers to the parameter sets associated with the one or more patient images, i.e. the determination rule allows the representation data sets to be determined in accordance with the associated one or more parameter sets. The representation data sets preferably depend not only on the associated parameter sets but also on the corresponding elements. In short, the representation data sets are thus determined on the basis of the corresponding elements and the associated one or more parameter sets by using the determination rule described by the atlas data. The element representation information preferably describes a plurality of representation data sets (two, three or more sets) for respective white atlas elements (in particular, for each white atlas element), and the determination rule describes how one of the plurality of representation data sets is selected for a respective white atlas element in accordance with the parameter set associated with the patient image to which the atlas image is to be matched. Each selection results in a determined grey atlas element. The determination rule is for example implemented using a reference table. Alternatively, a function is used, which is in particular dependent on a number (plurality) of parameters (referred to as "scanning parameters"). A grey value relationship is for example calculated on the basis of scanning parameters, such as for example the repetition time, magnetic field strength, etc., and tissue-dependent scanning parameters such as for example the T1 relaxation time, T2 relaxation time and proton density, by using a formula. The function can thus be used to calculate the representation data set (for example, a grey value relationship) in accordance with scanning parameters. The function is in particular designed to describe a continuous multitude of possible solutions for a representation data set (i.e. spanning the range of possible solutions), and the representation data set is calculated in accordance with the determination rule by selecting from this multitude of possible representation data sets. The determination rule in particular describes the scanning parameters which are to be selected and how they are to be used and the function for calculating the representation data set.

The method (in particular, a data processing method) in accordance with the invention also includes the step of determining a matching transformation for matching the patient image set and the atlas image set to each other. This matching transformation is referred to as an "AP transformation" (short for "atlas-patient transformation") if the atlas image is matched to the patient image. The matching transformation is determined by matching a respective image of the atlas image set and a respective image of the patient image set to each other. Matching can be performed by image fusion, which in particular uses similarity measures (see below) in order to find a matching transformation which optimally matches the respective images. The matching transformation can match one or more images of the atlas image set and one or more images of the patient image set. The respective image of the atlas image set and the respective image of the patient image set which are matched by the matching transformation are in particular associated with the same parameter set. Thus, the matching transformation is preferably determined by matching images which are associated with the same parameter set. The AP transformation in particular describes a deformation of atlas elements which is similar for all images of the atlas image set, wherein the images of the atlas image set are in particular associated with different parameter sets. This aspect is discussed in more detail below. The deformation is in particular similar if it is caused at least primarily by the deviation of the patient's anatomical structure from the general anatomical structure described by the atlas data and if the spatial properties of the patient images are similar. Any spatial distortion caused when generating the patient images is therefore preferably removed before the patient images and atlas images are matched.

In this application, the terms "image morphing" and/or "elastic fusion" are also used as an alternative to the term "image fusion", but with the same meaning.

Elastic fusion transformations (for example, image fusion transformations) are in particular designed to enable a seamless transition from one data set (for example, a first data set such as for example a first image) to another data set (for example, a second data set such as for example a second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. One or more (numerical) optimisation algorithms are preferably applied in order to find the transformation which results in an optimum degree of similarity. The degree of similarity is preferably measured by way of a measure of similarity (also referred to in this document as a "similarity measure"). The parameters of the optimisation algorithm(s) are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions in the one of the first and second images which is to be transformed, and the tips of the vectors lie at the corresponding voxel positions in the transformed image. A plurality of these vectors are preferably provided, for instance more than twenty or a hundred or a thousand or ten thousand, etc. There are preferably (other) constraints on the transformation (deformation), in particular in order to avoid pathological deformations (such as for instance all the voxels being shifted to the same position by the transformation). These constraints in particular include the constraint that the transformation is regular, which in particular means that a Jacobian determinant calculated from a matrix of the deformation field (in particular, the vector field) is larger than zero. The constraints also in particular include the constraint that the transformed (deformed) image is not self-intersecting and in particular that the transformed (deformed) image does not comprise faults and/or ruptures. The constraints also in particular include the constraint that if a regular grid is transformed at the same time as the image and in a corresponding manner, the grid is not allowed to interfold at any of its locations. The optimisation problem is in particular solved iteratively, in particular by means of an optimisation algorithm which is in particular a first-order optimisation algorithm, in particular a gradient descent algorithm. Other examples of optimisation algorithms include optimisation algorithms which do not use derivations, such as the downhill simplex algorithm, and algorithms which use higher-order derivatives, such as Newton-like algorithms. The optimisation algorithm preferably performs a local optimisation. If there are a plurality of local optima, then global algorithms such as simulated annealing or genetic algorithms can be used. In the case of linear optimisation problems, the simplex method can for instance be used.

In the steps of the optimisation algorithms, the voxels are in particular shifted by a magnitude in a direction, such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation (for example, a matching transformation) can in particular be used to determine a degree of similarity (also referred to as a "measure of similarity" or "similarity measure") between the first and second data sets (images). Optimum matching can for instance be defined (predetermined) as matching which results in at least a predetermined measure of similarity. To this end, the deviation between the elastic fusion transformation and an identity transformation is determined. The degree of deviation can for example be calculated by determining the difference between the determinant of the elastic fusion transformation and the identity transformation. The higher the deviation, the lower the degree of similarity. The degree of deviation can thus be used to determine a measure of similarity.

A measure of similarity can in particular be determined on the basis of a determined correlation between the first and second data sets.

The matching transformation referred to as an AP transformation preferably describes a matching transformation which matches one or more atlas images to one or more patient images, i.e. the AP transformation is preferably applied to atlas images in order to determine matched atlas images.

In an AP transformation, the spatial information (position and/or geometry) of the patient elements represented in the patient image preferably remains fixed, while the spatial information (position and/or geometry) of the atlas elements in the atlas images is changed so as to match the spatial information of the patient elements in the patient images when the AP transformation is applied. The image which results from applying the AP transformation to the atlas image is referred to as the matched atlas image. The AP transformation is preferably designed to maintain the segmented structure of the atlas, i.e. to maintain the corresponding elements such that deformed corresponding elements are shown in the matched atlas image. Preferably, the representation of the deformed corresponding elements in the matched atlas image respectively corresponds to the representation data sets determined for the respective (unmatched) corresponding elements, i.e. the matching transformation preferably only acts on the spatial information and not on representation information described by the representation data sets, in accordance with this embodiment. In accordance with another embodiment, the representation information determined by the representation data set is adapted in view of the representation of patient elements or patient images. In accordance with yet another embodiment, at least some of the representation of at least some of the grey atlas elements is determined on the basis of the representation of patient elements, particularly if it is not possible to determine representation data sets. The patient elements are preferably identified by applying the AP transformation, which allows the patient image to be segmented into patient elements. The representation of the patient element is then determined and used in turn to determine the representation of the matched grey atlas elements of the matched atlas image.

In accordance with an alternative embodiment, the matching transformation is referred to as a PA transformation and preferably describes a matching transformation which matches one or more patient images to one or more atlas images, i.e. the spatial information (position and/or geometry) of the atlas elements represented in the atlas images remains fixed, while the spatial information (position and/or geometry) of the patient elements in the patient images is changed to match the spatial information of the atlas images in the atlas images when the PA transformation is applied. This transformation can in particular be used to improve atlas data which are to be improved (improved atlas data are referred to as "model data") by adding information from patient images to the model data. The PA transformation can be used as described in the parallel application, filed by the same applicant, entitled "Determining an Anatomical Atlas". The PA transformation corresponds to the PM transformation discussed in said parallel application and is used to improve the atlas data by means of patient data.

The step of determining the atlas image set preferably comprises the step of determining the representation data sets for the corresponding elements. The element representation information preferably describes a plurality of representation data sets for at least one (in particular, two or more) of the white atlas elements, preferably most of the white atlas elements and in particular all of the white atlas elements, i.e. the element representation information allows one of the respective plurality of representation data sets to be determined for a white atlas element in accordance with one of a respective plurality of different parameter sets by using the determination rule.

If a particular parameter set is described by the patient data for a particular patient image, then representation data sets for each of the corresponding elements are preferably determined in accordance with said particular parameter set. In particular, one of the representation data sets is selected from the plurality of representation data sets described by the element representation information for each of the corresponding elements by using the determination rule which in particular describes the representation data set which is to be selected for each of the corresponding elements in accordance with the particular parameter set described by the patient data for said particular patient image. If the patient data describe more than one parameter set and more than one patient image, then this process is preferably performed for each of the patient images. Preferably, more than one representation data set is selected from the plurality of representation data sets described by the element representation information in accordance with the determination rule and the plurality of parameter sets described by the patient data for more than one patient image, in order to allow more than one atlas image to be determined, i.e. for each of the corresponding elements. For each of the corresponding elements, the number of selected representation data sets preferably corresponds to the number of patient image sets if there is a different representation of the atlas element for each of the parameter sets described by the patient data. The determination rule preferably refers to the same parameter set for all of the corresponding elements of an atlas image, i.e. the parameter set of the patient image to which the atlas image is to be matched (or vice versa). Thus, an atlas image is preferably associated with only one parameter set.

The determination rule in particular comprises an assignment rule for respectively assigning one representation data set to one corresponding element for each different parameter set. The assigned representation data set describes the representation of the corresponding element in the atlas image associated with one of the different parameter sets. The assignment rule preferably depends on the parameter set which is associated with the patient image which includes the patient element to which the corresponding element is to be matched.

In accordance with one embodiment, the determination rule comprises assignment rules for (all of) the respective white atlas elements, so that there is an assignment rule for each of the white atlas elements to be matched, i.e. for each of the corresponding elements. In accordance with preferred embodiments, the assignment rule is simplified by not providing an assignment rule for each of the atlas elements but rather for classes of atlas elements, referred to as representation classes (or also "tissue classes"), and preferably assigning (each of) the respective atlas elements to one of the representation classes. This reduces the processing load of the data processing method. For each of the white atlas elements belonging to the same respective representation class, the same representation data set is preferably determined for each of the respective parameter sets. In other words, different grey atlas elements belonging to the same representation class are represented in an atlas image in accordance with the same representation data set, irrespective of the individual parameter set associated with the atlas image which includes the different grey atlas elements. Further details with respect to representation classes are given below.

The representation (representation properties) of the corresponding elements in the one or more atlas images is/are determined on the basis of the determined representation data sets. Each of the corresponding elements represented in the one or more atlas images is in particular represented in accordance with the assigned representation data sets. All the corresponding elements of a respective atlas image are preferably associated with the same parameter set.

The representation data sets can represent rules for defining absolute values of representation, such as an absolute image value (for example, an absolute grey value or an exact position in a colour space) which is in particular used for the whole space occupied by a grey atlas element. The representation data sets can also describe relative rules for representation (in particular, for the representation of image values), such as for instance that one particular atlas element should be represented with a lower grey value than another particular atlas element or that a colour value is shifted in a particular direction from one atlas element to another. The parameter sets can also represent incomplete information (at least for some of the corresponding elements) which does not allow a representation data set to be determined directly for all of the corresponding elements (for example by simply using a reference table). The parameter set can for example be incomplete in that it is not known whether a contrast agent was injected into the patient before the patient image was generated or not. The representation of a corresponding element which can be influenced in terms of its representation by a contrast agent will then be uncertain. Flexibility in determining the representation of one or more of the corresponding elements is then desirable. This is preferably achieved by performing a first matching process (using image fusion) and comparing the matched atlas images with the patient images. The first matching process relies in particular on spatial properties only, in particular with respect to the corresponding elements for which a representation data set has not yet been determined. This first matching process in particular allows the patient image to be segmented into patient elements. On the basis of the comparison, the representation of the corresponding elements is changed so as to be closer to the representation of the corresponding patient elements in the patient images. In the next step, the matching transformation is correspondingly adapted such that applying the matching transformation to the atlas images (i.e. a second matching process) results in matched atlas images in which the representation of corresponding elements is more similar to the representation of the corresponding patient elements in the patient images than it was after the first matching process but before the second matching process. Thus, the determination rule preferably uses information on the representation of the patient elements in the patient images in order to determine the representation of the matching elements. This information is referred to as patient image representation data, which in particular describe the image values which represent the patient elements.

The term "similar" as used here generally covers the two meanings of "similar but not identical" and "similar and identical", i.e. the term "similar" in particular also covers the term "identical". The above-mentioned similarity measure can be used to quantify the term "similar", and a predetermined threshold for the similarity measure can be applied in order to differentiate between what is similar and what is not similar.

As mentioned above, the patient images can be associated with different parameter sets, wherein anatomical elements of the patient represented by one or more of the patient elements in the patient images associated with different parameters are in particular identical. If, for example, a CT image and an MR image of a patient element (for example, the lung) are provided, then a matching transformation which deforms an atlas element to match a patient element associated with a parameter set and a matching transformation which transforms the atlas element to match the patient element represented in another patient image associated with another parameter set will perform a similar spatial deformation if there is no geometric distortion incurred by the analytical devices or if the incurred distortion is similar in each case. The matching transformation is preferably designed to match one of the atlas images to one of the patient images associated with one of the parameter sets and another of the atlas images with another of the patient images associated with another of the parameter sets. Determining the part of the matching transformation which matches one of the atlas images and one of the patient images, both of which are associated with the same parameter set, to each other preferably involves taking into account information on another part of the matching transformation which matches another of the atlas images and another of the patient images, which are associated with another of the associated parameter sets, to each other. Thus, information resulting from different matching processes (relating to different parameter sets) is used reciprocally in order to improve the quality of matching. The reciprocally used information is in particular spatial information. Preferably, a spatial correlation between patient images associated with different parameter sets is determined before this reciprocal information is used. Atlas images and patient images are for example rigidly matched to each other, in particular in order to establish a common spatial reference system for all the patient images, in particular so that deformation vectors relating to different matching processes can be determined. As mentioned above, the matching transformation preferably performs different matching processes, i.e. matches atlas images and patient images associated with different parameter sets, wherein the images comprises common patient elements (of the same patient).

The matching transformation (in particular, the AP transformation) is generally determined in such a way that (first) spatial information on matching one of the atlas images (a first atlas image) and one of the patient images (a first patient image) to each other (in particular, information on matching one of the atlas images to one of the patient images) is used to determine how another of the atlas images (a second atlas image) and another of the patient images (a second patient image) are matched to each other. The former matching process is preferably described by a first part of the matching transformation, while the latter matching process is preferably described by a second part of the matching transformation. The first atlas image and first patient image which are subjected to the former (first) matching process are associated with a first parameter set, while the second atlas image and second patient image which are subjected to the latter (second) matching process are associated with a second (different) parameter set. Thus, the first spatial information is used as a basis for determining the second part of the matching transformation (in particular, the second part of the AP transformation) which matches another of the atlas images and another of the patient images to each other, i.e. one part of the matching transformation which relates to one of the parameter sets uses information (in particular, spatial information) from another part of the matching transformation which performs matching with respect to another parameter set.

As mentioned above, the spatial deformation represents an example of the information used in this way. The information can in particular be used reciprocally, i.e. reciprocal information is used. In order to apply the reciprocal information, the matching transformation is varied on the basis of the reciprocal information, and the quality of the matching transformation for different variations is determined. Preferably, the variation which results in the highest-quality matching transformation is selected. In order to determine the quality of the matching transformation, the quality of a matching process between a patient image and an atlas image is in particular determined. The matching quality can be determined on the basis of the degree of similarity (for example, quantified by the similarity measure) between the images after matching has been performed. If the matching transformation is determined by applying the same spatial changes (change in position and/or geometry) to one of the first atlas image and first patient image (in particular the first atlas image in the case of AP transformations) and one of the second atlas image and second patient image (in particular the second atlas image in the case of AP transformations), then the deformation can be varied by varying the transformation, and the kind of transformation which is determined as the matching transformation is the one which on average (for example, by averaging a similarity measure determined for a first AP sub-transformation APT1 and a similarity measure determined for a second AP sub-transformation) results in the greatest similarity between the respective atlas images and the respective patient images.

In accordance with one embodiment, the matching transformation comprises parts which are distinct matching sub-transformations. The matching sub-transformations are preferably coupled, since spatial information—in particular, properties of the matching sub-transformations (such as the deformations determined by the matching sub-transformation)—have an influence on each other. The respective matching sub-transformations respectively match the atlas images associated with a respective associated parameter set and a respective patient image associated with the same respective associated parameter set, i.e. each matching sub-transformation is directed to a matching process relating to one of the parameter sets. The matching sub-transformations are in particular AP sub-transformations which respectively match one atlas image to one patient image. The matching sub-transformations are in particular coupled in that they each influence the determination of the other. One of the matching sub-transformations is in particular determined on the basis of determining another of the matching sub-transformations. This coupling is in particular based on a spatial correlation between atlas images and patient images associated with different parameter sets. As mentioned above, the correlation can in particular be established by means of rigid transformations applied with respect to the different parameter sets. The spatial correlation between the atlas images in particular is preferably known, since they represent the same (part of) the general anatomical structure, i.e. the same spatial information. The representation of the structure (in particular its visual appearance) in the atlas images can differ in accordance with the associated parameter sets.

As mentioned above, representation classes are preferably used to classify the atlas elements. Each atlas element is preferably assigned to one of the representation classes. The representation classes define the representation of the atlas elements for different parameter sets. The atlas elements are preferably assigned to the representation classes surjectively. The determination rule preferably uses the assignment between atlas elements and representation classes to describe an assignment between atlas elements and representation data sets. This advantageously simplifies the assigning process, since a number of in particular different atlas elements (such as for example one, two or more atlas elements, in particular different atlas elements) can preferably be assigned to the same representation class. Preferably, each of the representation data sets describes the representation of one particular atlas element which is associated with one parameter set. If particular atlas elements belong to the same representation class, then the same representation data set is determined for all of these particular atlas elements by the determination rule, providing they are associated with the same parameter set. If one or more representation data sets is/are respectively associated with one or more parameter sets for a particular representation class, then the one or more representation data sets represent a subset of a plurality of representation data sets. The subset is defined within the particular representation class and is selected by the determination rule for an atlas element belonging to said particular representation class. Thus, a representation class represents a subset of the representation data sets. The determination rule assigns a particular representation data set of the subset to an atlas element belonging to the representation class in accordance with the parameter set. In other words, the respective representation classes represent respective subsets of the plurality of representation data sets, and for each representation class, there is a characteristic bijective assignment between the representation data sets of the subset and the parameter sets, i.e. for each representation class, the determination rule assigns one representation data set (of the subset) to an atlas element belonging to the representation class, wherein the assignment is made in accordance with the parameter set associated with the patient image comprising the patient element to which the atlas element is to be matched.

As mentioned above, the representation data sets describe the representation (also referred to as the "representation property"), in particular the visual appearance, of anatomical elements in an atlas image. In particular, the representation data set can for example describe (as an example of a representation property) image values, in particular a single image value for a particular anatomical element or a single average value for the region (in particular, area) occupied by the anatomical element. The image value can for example be a grey value, an intensity value, a colour value, a value in a colour space, etc. The representation data set can also describe (as an example of a representation property) a lower limit and/or upper limit of the image values, for instance a range of grey values or a range in the gamut of the colour space for a particular anatomical element (in particular, for each of the representation classes). The representation data set in particular describes (as an example of a representation property) a relationship between image values of different anatomical elements, for instance that a grey value is higher in one anatomical element than in another anatomical element. Any such description refers of course to a particular parameter set. With respect to another parameter set, the relationship may be different. The relationship can of course also be in the colour space and consist for instance of the fact that the intensity is higher for one anatomical element than for another or that there is a shift in the colour space in a particular direction if the image value of one anatomical element is compared with the image value of another anatomical element. Aside from the aforementioned average of image values for the anatomical elements (associated with particular parameter sets), a standard deviation from the average image values can be described by the representation data sets. Structures of modulations of the image values can also be described (as an example of a representation property) for the anatomical elements by the representation data sets. Spatial modulations of image value variations within the anatomical element can for example be described (for instance by means of DCT coefficients). Characteristics of transitions between representations of different anatomical elements can also be described (as an example of a representation property). The transition from a bone structure to a soft tissue structure is for example different in an x-ray image as compared to an MRT image. In particular, the representation property does not comprise spatial information, hence the representation data set in particular does not describe spatial information. The representation property is also referred to as "representation information".

The above-mentioned representation classes are in particular substance classes (also referred to as "tissue classes"), since anatomical elements which are of a similar substance can be represented by the same subset of representation data sets, wherein each member of the subset is respectively assigned to one of the parameter sets. An anatomical element consisting mainly of a particular substance (for instance, fat or bone) will for example have the same representation (in particular, visual appearance), irrespective of where the anatomical element is located in the patient's body. Thus, in accordance with one embodiment, information on the substance of an anatomical element is used to assign the anatomical element to one of the representation classes.

As mentioned above, the atlas data comprise atlas spatial information which describes spatial information (i.e. position and/or geometry) for the general anatomical structure. In accordance with one embodiment, the spatial information is static, i.e. the position and/or geometry of the general anatomical structure is fixed for all elements. In accordance with a preferred embodiment, the spatial information is flexible, i.e. the position and/or geometry of one or more of the atlas elements is flexible. The term "flexible" as used here means in particular that a variation in the position and/or geometry is allowed in order to improve the quality of the matching process. As mentioned above, the matching quality can be measured by determining the degree of similarity (by means of a similarity measure) between the element (for example, an atlas element) which is subjected to the matching transformation and the element (for example, a patient element) to which the transformed element is to be matched.

There are in particular anatomical elements which can significantly vary in terms of their position from patient to patient. The flexibility information can accordingly include a statistical probability for different positions and/or geometries of the anatomical element. The position of the kidney can for example vary from patient to patient. For the purposes of this document, an organ is not generally an anatomical element but can comprise different anatomical elements, since an organ can consist of regions occupied by different types of substances. Conversely, an anatomical element may be larger than an organ. The brain stem, for example, is only part of the white matter but is not clearly separated from other parts of the white matter. In accordance with one embodiment, organs which cannot be clearly differentiated from other organs, such as the brain stem, are identified as a sub-structure within an anatomical element. Preferably, an anatomical element consists at least predominantly of one or more substances which manifest themselves through the same representation property in analytical images associated with different parameter sets, i.e. the one or more substances belong to the same representation class.

The above-mentioned flexibility information which can be part of the atlas spatial information is in particular used as a constraint when determining the matching transformation. The anatomical variability of the position of anatomical elements as mentioned above represents one reason for the use of flexibility information. Another reason is changes in the position of anatomical elements due to intentional changes in position brought about by the patient or a user (such as for example medical staff). The arms and legs of a patient can for example adopt different positions with respect to the patient's torso. The variability of these possible positions, in particular due to the variability of the extremities of the patient's body, can also form a basis for the flexibility information. Another reason for using flexibility information can be the different positions of organs (and therefore anatomical elements) due to the different sizes of the lung(s) during a breathing cycle or due to the heart beat or other, unintentional movements.

Anatomical variability can also be due to a pathological change in the patient's body. The development of a tumour can for example shift parts of the brain.

The flexibility information can in particular also comprise a constraint with respect to positions and positional changes such as rotations. A rotation of one vertebra with respect to another by more than 180° is for example anatomically impossible and can accordingly be excluded by means of the flexibility information.

The expression "acquiring data" encompasses in particular (within the framework of a data processing method) the scenario in which the data are determined by the data processing method or program. Determining data in particular encompasses measuring physical quantities and transforming the measured values into data, in particular digital data, and/or computing the data by means of a computer and in particular within the method of the invention. The meaning of "acquiring data" also in particular encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. In particular, the acquiring step does not involve an invasive step which would represent a substantial physical interference with the body requiring professional medical expertise to be carried out and entailing a substantial health risk even when carried out with the required professional care and expertise. Acquiring—in particular, determining—data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe which is preferably called "XY information".

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit or CPU) which executes the computer program elements, and optionally a volatile memory (in particular, a random access memory or RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The method in accordance with the invention is preferably at least partly executed by a computer, i.e. all the steps or merely some of the steps (i.e. less than the total number of steps) of the method in accordance with the invention can be executed by a computer.

The object stated at the beginning is achieved by the subject-matter of any of the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically sensible and feasible. A feature of one embodiment which is functionally identical or similar to a feature of another embodiment can in particular replace said latter feature. A feature of one embodiment which supplements a function of another embodiment can in particular be added to said other embodiment.

Pathological Changes

As mentioned above, the method described here can also be applied if the patient images describe an anatomical structure which exhibits pathological changes. This can be handled using the above-described flexibility information. In accordance with another embodiment described in the following, parameters referred to as "patho parameters" are used to determine and in particular select information on the general anatomical structure which fits the anatomical structure of the patient which exhibits pathological changes. More specifically, the patho parameter specifies and in particular classifies the pathological changes to the anatomical structure, i.e. the general anatomical structure as compared to a healthy patient and the anatomical structure of the patient as compared to a healthy patient. The patho parameter in particular specifies the anatomical structure in accordance with a medical classification system such as the TNM Classification of Malignant Tumours. The data processing method is preferably embodied by the following method:

A data processing method for determining a matching transformation for matching an image of an anatomical body structure of a patient, referred to as a patient image, and an image of a general anatomical structure, referred to as an atlas image, wherein both the anatomical body structure of the patient and the general anatomical structure exhibit pathological changes and the patient image is associated with one of a plurality of different parameters which are referred to as patho parameters and specify the pathological changes in accordance with a classification, the method comprising the following steps performed by a computer:
  acquiring atlas data which contain information on a description of a plurality of images of the general anatomical structure for a plurality of patho parameters and in particular spatial meta information on the pathological changes; and
  acquiring patient data, comprising the sub-steps of
    acquiring the patient image, and
    acquiring the patho parameter associated with the patient image set;
  determining, on the basis of the atlas data and the patient data, the atlas image which represents at least a part of the general anatomical structure which exhibits pathological changes in accordance with the patho parameter; and determining the matching transformation which matches the atlas image and the patient image and in particular matches the spatial meta information to the patient image.

The above-described method represents an alternative and independent method of an alternative and independent invention. The above-described method is preferably combined with the method described in the independent claims(s) or any of the dependent claims. As described above, atlas data are acquired which contain information on a description of a plurality of images of the general anatomical structure for a plurality of patho parameters, i.e. each image of the plurality of images specifies a particular general anatomical structure which exhibits a particular pathological change. The information on the description is in particular the image (atlas image) of the general anatomical structure which is associated with the particular patho parameter and/or can be spatial information on the general anatomic structure as described above which is associated with the particular patho parameter and/or can be element representation information as described above which is associated with the particular patho parameter. In accordance with another step of this alternative method, the patient data are acquired. The patient data comprise at least one patient image which is associated with a particular patho parameter. This allows the information on the description of one of the plurality of images of the general anatomical structure, which exhibits the pathological changes specified by the particular patho parameter, to be determined. If the information on the description is an atlas image, then the atlas image is determined by selecting the atlas image which is associated with the particular patho parameter. In a following step, the matching transformation which matches the atlas image and the patient image to each other and in particular matches the atlas image to the patient image (both of which are associated with the same patho parameter) is determined.

As mentioned above, the alternative method can be combined with the method described above. In particular, the atlas data describe the spatial information on the general anatomical structure for a plurality of different patho parameters. The spatial information of atlas elements can in particular vary in accordance with the patho parameters, for example due to deformation caused by tumours. The element representation information also varies in accordance with the patho parameters. In particular, a spatial distribution of representation information within the different anatomical elements (atlas elements) varies in accordance with the patho parameters. The spatial distribution of the representation information in particular represents an average spatial distribution of pathological changes associated with the respective patho parameter. In addition to the element representation information or as an alternative to the element representation information, meta data referred to as patho meta data can be acquired. The patho meta data describe meta information on pathological changes to the general anatomical structure associated with a particular patho parameter. This meta information can in particular be a statistical probability distribution for the presence of pathological changes within the respective atlas elements (in particular, a spatial statistical distribution of such a probability which depends on positions or sub-regions within the atlas element) and/or can be information on an average geometry of distinct pathological changes (distinct tumours) and/or can be information on an average number of distinct pathological changes and variations of said number. In particular, the matching transformation can transform (and in particular deform) the spatial statistical probability distribution associated with the atlas image onto the patient image by using the matching transformation, i.e. the spatial statistical probability distribution of pathological changes represents spatial meta information on the pathological changes which is matched to the patient image. The spatial statistical distribution is an example of spatial meta information.

If, for example, the atlas data only contain spatial information on the general anatomical structure and the spatial meta information, then the spatial properties of the white atlas elements to be matched to the patient image are determined on the basis of the patho parameter, and the spatial meta information for the white atlas elements is determined on the basis of the patho parameter. The spatial statistical probability distribution can for instance be described by a two-dimensional or three-dimensional contour line model. This model is deformed in accordance with the deformation of the spatial properties of the atlas elements when the atlas element (the white atlas element combined with the spatial meta information) is matched to the patient image.

Additional features of the invention are disclosed in the following description of embodiments. Different features of different embodiments can be combined.

BRIEF DESCRIPTION OF THE FIGURES

FIGS. 1A, 1B, 1C, and 1D show the steps of the data processing method in one embodiment of the present invention.

DETAILED DESCRIPTION

Figure 1A:
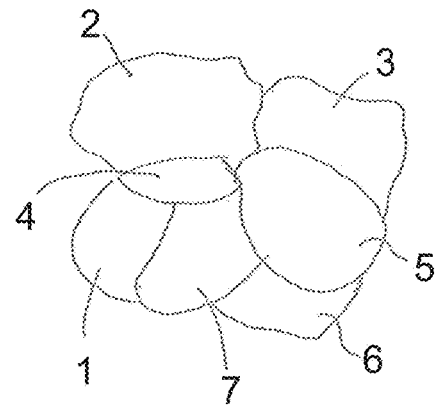
Figure 1A:
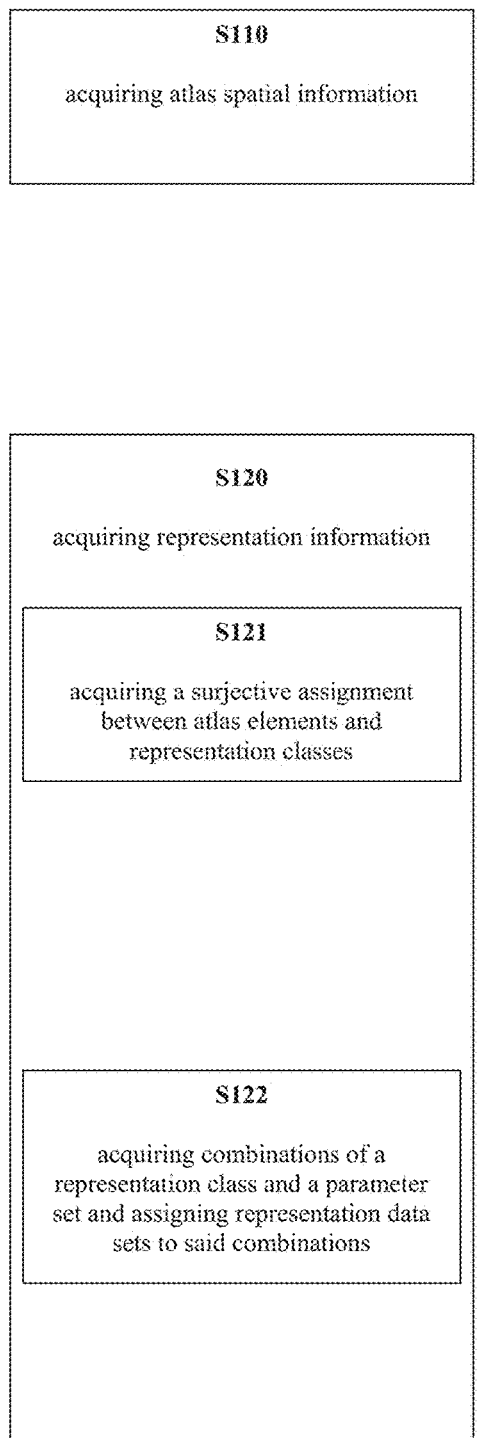

FIGS. 1A, 1B, 1C, and 1D show the steps of an embodiment of the data processing method of the present invention. The individual steps and/or sub-steps of this embodiment are described on the left-hand side in FIGS. 1A, 1B, 1C, and 1D. Explanatory drawings pertaining to the individual steps are respectively shown on the right-hand side in FIGS. 1A, 1B, 1C, and 1D, i.e. each of the explanatory drawings refers to the method step directly to the left of it.

In a first step S110, atlas spatial information is acquired. The atlas spatial information describes the geometry of the atlas elements and their relative position. The accompanying explanatory drawing illustrates the geometry and relative position in two-dimensional space of seven atlas elements 1 to 7. The atlas is preferably three-dimensional.

Further below in FIG. 1A, Step S120 begins with the sub-step S121. In the course of Step S120, representation information is acquired. Acquiring the representation information preferably involves acquiring an assignment between atlas elements and representation classes (Sub-step S121). The use of representation classes allows the data processing load to be reduced and in particular reflects the physical property of an anatomical body that different anatomical elements can consist of the same substance (tissue). As shown in Table 1 to the right of Sub-step S121, each of the atlas elements 1 to 7 is assigned to one of the representation classes A, B, C and D. The atlas element 1 is for example assigned to the representation class A, the atlas element 5 is assigned to the representation class D, and the atlas element 7 is assigned to the representation class B. Since the atlas element 2 is also assigned to the representation class B, assignment is preferably surjective, i.e. different atlas elements can be assigned to the same representation class. This reduces the processing load.

Sub-step S122 is shown at the bottom left of FIG. 1A. In this sub-step, representation data sets are assigned to combinations of a representation class and a parameter set. The representation data set a is for example assigned to a combination of the representation class A and the parameter set α. Preferably, all or at least most of the possible combinations of representation classes and parameter sets are assigned one of the representation data sets. An example of such an assignment is shown in Table 2. Thus, for example, the atlas element 5 is assigned to the representation class D, as shown in Table 1, and the representation class D is represented in accordance with the representation data set c if the parameter set is α and/or is represented in accordance with the representation data set d if the parameter set is β and/or is represented in accordance with the representation data set i if the parameter set is γ. This reflects the fact that anatomical elements can be represented differently, depending on the parameter set (for example, the image modality).

Sub-step S123 is shown at the top left of FIG. 1B. In Sub-step S123, the description of the representation data set is acquired, i.e. representation information which in particular describes the visual appearance of an anatomical element (except for spatial information such as geometry and/or size) is described. In the given example, the representation data set c features horizontal, parallel lines as an example of a visual appearance. The lines shown in the right-hand column of Table 3 are intended to represent for example the different grey values in an anatomical image generated by an analytical device. The letters in the left-hand column of Table 3 can for instance represent particular grey values.

In addition to the aforementioned sub-steps S121, S122 and S123, an additional sub-step S124 within Step S120 is also shown, in which a determination rule is acquired. It should be noted at this juncture that the sequence of method steps shown in FIGS. 1A and 1B is not obligatory.

Sub-step S124 relates to the step of acquiring the determination rule. In accordance with one embodiment, the determination rule describes how a representation class is selected for an atlas element using a table which assigns atlas elements to respective representation classes. When applying the rule, the corresponding elements have preferably already been identified, such that the representation classes assigned to the corresponding elements are determined in a first sub-step of the determination rule (using Table 1). In accordance with a second part of the determination rule, the representation class selected for the corresponding element and the parameter set associated with the patient image (to which the atlas image is to be matched) are used to determine the representation data set (using Table 2). The representation data sets for the corresponding elements are thus determined in the second sub-step of the determination rule.

A third part of the determination rule stipulates that the representation information corresponding to the representation data set can be acquired for instance by using a table in order to allow particular representation information to be assigned to the respective corresponding elements when the determination rule is to be applied (see Sub-step S143).

In short, the determination rule in particular regulates the way in which the representation information for the atlas elements is to be determined when the corresponding elements and the parameter sets are known.

Figure 1C:
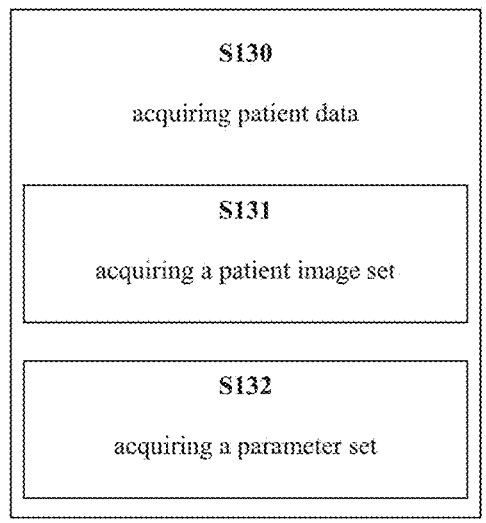
Figure 1C:
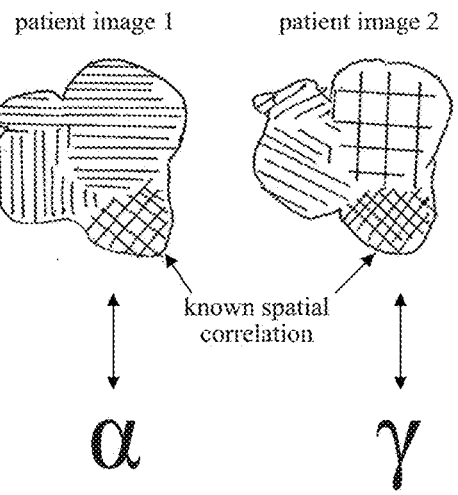
Figure 1C:
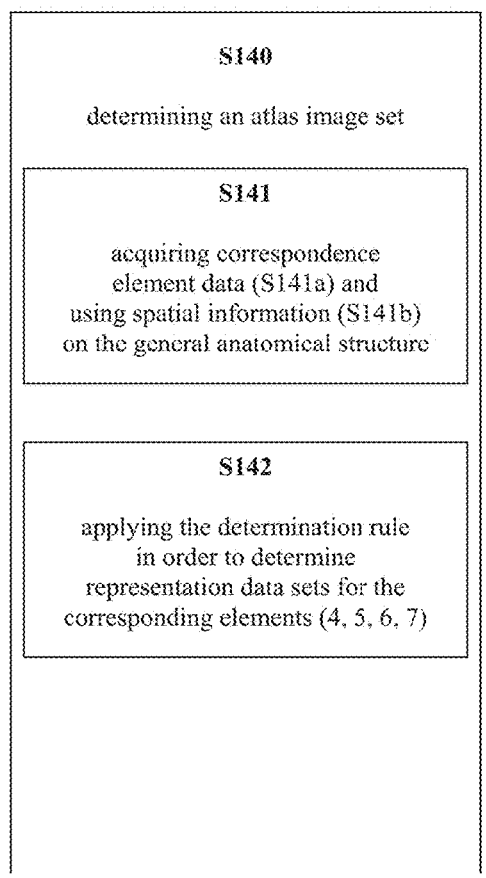
Figure 1C:
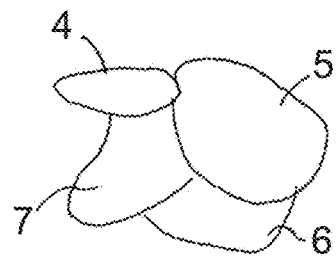
Figure 1D:
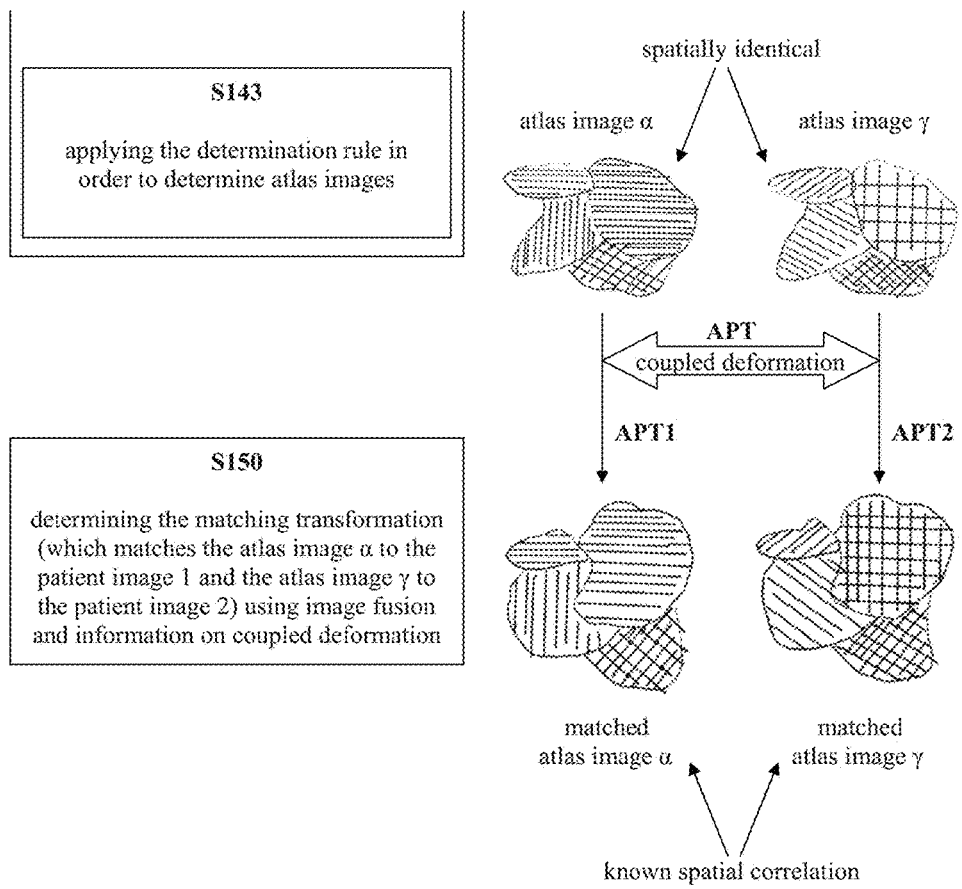

The step of acquiring patient data is shown at the top left of FIG. 1C. This step S130 comprises two sub-steps S131 and S132. The first sub-step S131 relates to acquiring a patient image set. In the example given at the top right of FIG. 1C, the patient image set comprises a patient image 1 and a patient image 2. A parameter set is respectively assigned to each of the patient images, i.e. the parameter set α is assigned to patient image 1, and the parameter set γ is assigned to patient image 2.

The patient data preferably also comprise information on the spatial correlation between the patient images in the patient image set. The spatial correlation is in particular known. It is for example known that the spatial information is identical, i.e. the geometry and size of the anatomical elements shown in the patient image and their relative position is identical, or that the deviations from such identity are negligible. In accordance with an alternative embodiment, the patient images are not identical, but a spatial transformation is known which allows the spatial information of one patient image to be transformed into the spatial information of another patient image. One of the analytical devices may for example generate a known spatial distortion which can be described by a spatial transformation. Even if the spatial distortion is not known, spatial distortions usually have a low spatial frequency, such that it is preferably assumed that high spatial frequency information included in the patient images is identical.

In addition to the patient image sets acquired in Sub-step S131, parameter sets are preferably also acquired in Sub-step S132. In the example given to the right of Sub-step S132, the parameter set α is acquired for the patient image 1, and the parameter set γ is acquired for the patient image 2.

The aforementioned data acquisition steps S110, S120 and S130 can be performed in parallel or sequentially. The atlas image set is then determined in Step S140.

Step S140 preferably comprises the sub-step S141 in which the correspondence element data are acquired. The correspondence element data describe the atlas element which corresponds to the structure shown in the patient images of the patient image set, i.e. the atlas elements which have corresponding patient elements in the patient images and are to be the subject of a matching transformation. In the example given, the correspondence element data describe the atlas elements 4, 5, 6 and 7 as being corresponding elements.

In another part of S140, namely Sub-steps S142 and S143, the determination rule is applied in order to determine the atlas images. To this end, the representation data sets are determined for each of the corresponding elements 4, 5, 6 and 7 and for each of the atlas images α and γ by referring to Tables 1 and 2, i.e. Table 1 indicates the representation class C for the atlas image α and the corresponding element 4, and Table 2 indicates the representation data set c for the representation class C and the parameter set α. As can be seen from the table at the bottom right of FIG. 1C, the corresponding elements 4 and 5 have the same representation data set in the atlas image α but different representation data sets in the atlas image γ, i.e. the atlas elements 4 and 5 can only be differentiated in the atlas image γ. As can also be seen from the patient images 1 and 2, only patient image 2 shows different grey values between the top left and top right of the image.

Since the atlas images α and γ are generated from the same atlas, the spatial information (geometry and size) of the atlas image α is identical to the spatial information of the atlas image γ.

In a subsequent step S150, the matching transformation is determined. In the example shown in FIG. 1D, the matching transformation is an AP transformation which matches the atlas image α to the patient image 1 and the atlas image γ to the patient image 2. The spatial correlation between the patient image 1 and the patient image 2 is preferably known. In the example given, the spatial information of patient images 1 and 2 is identical, i.e. the atlas images α and γ undergo the same deformation. This is an example of coupled deformation. As mentioned above, the corresponding elements 4 and 5 have the same representation data set for α but different representation data sets for γ. This allows the corresponding elements 4 and 5 to be segmented even for the matched atlas image α, since the deformation is coupled and the spatial information of the matched corresponding element 5 in the matched atlas image α is therefore the same as the spatial information of the matched corresponding element 5 in the matched atlas image γ, i.e. the spatial information of bone structures in a CT image can for example be used in order to identify the corresponding structures in an MR image, while conversely, the spatial information on anatomical elements consisting of soft tissue as provided by MR images can be used to determine the corresponding matched atlas elements in a matched atlas image representing a CT image.

The aforementioned AP transformations (APT1 and APT2) can be determined simultaneously or iteratively. If iteratively determined, a first trial APT1 is for example determined which results in a best match between the atlas image α and the patient image 1. Information on deformation is extracted from the first trial APT1. The deformation from the first trial APT1 is then applied when matching the atlas image γ to the patient image 2 by means of a first trial APT2. The first trial APT2 is then varied by varying the deformation, in particular within a predetermined range. If a varied deformation results in a better match, then this varied deformation is used to determine a second trial APT1. The second trial APT1 uses the varied deformation to match the atlas image α to the patient image 1. Again, the second trial APT1 can be varied by varying the deformation, in particular within a predetermined range, in order to determine another modified deformation which can then in turn be applied in order to determine a second trial APT2. This process can be repeated until varying the deformation no longer improves the averaged matching quality for APT1 and APT2. Instead of the sequential determination approach described above, a simultaneous determination approach is also possible and represents another preferred embodiment.

In accordance with one embodiment, the deformations described by APT1 and APT2 are described by using deformation vectors and establishing a common reference system for APT1 and APT2 (for example, by way of a preliminary rigid transformation as mentioned above). In accordance with one embodiment, the deformation vectors determined for APT1 and APT2 are added in a first iterative step of determining the matching transformation, i.e. a first deformation vector for describing the deformation of a part of the atlas image α by APT1 and a second deformation vector for describing the deformation of a part of the atlas image γ by APT2 are for example provided. These deformation vectors for the atlas image α and the atlas image γ preferably originate at the same spatial point or region in a common reference system. Usually, fusion algorithms result in a deformation vector of 0 if no clear information on deformation can be found. If the deformation can only be reliably determined from one of the transformations APT1 and APT2, then adding the deformation vectors means that the determination is primarily based on the part of the matching transformation which provides the most information. The deformation described by the matching transformation is therefore preferably weighted in accordance with the amount of image information (described for instance by image energy or contrast) available in at least one of the patient image and atlas image, preferably the patient image. The matching transformation is preferably determined for all or at least most of the parts of the images in the way described above, by determining a plurality of deformation vectors for each transformation.

Figure 2:
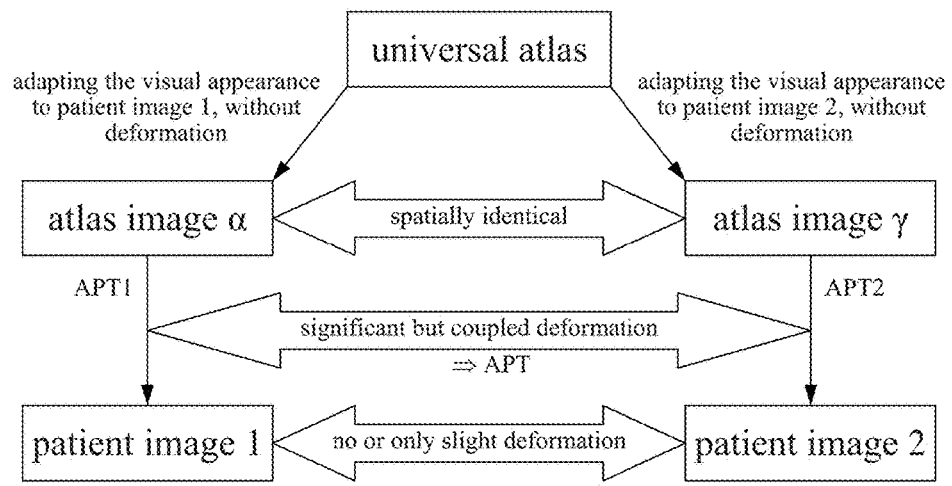
FIG. 2 shows a flow diagram which illustrates and explains correlated matching.

FIG. 2 schematically shows and describes an embodiment of the present invention.

The universal atlas describes the general anatomical structure and is used to determine an atlas image α and an atlas image γ. The atlas images α and γ are spatially identical, but their representation information is respectively adapted in accordance with the parameter set of the patient image to which each atlas image is to be matched, i.e. the visual appearance of the atlas image α is adapted so as to approach the visual appearance of the patient image 1 by using the parameter set associated with the patient image 1, and the representation information of the atlas image γ is determined on the basis of the parameter set associated with the patient image 2 in order to approach the visual appearance of the patient image 2. The matching transformation APT is then determined which can comprise sub-transformations APT1 and APT2 which are coupled with respect to the spatial information, in particular with respect to deformation. If, in particular, the patient images 1 and 2 exhibit the same spatial information or there is only a slight deviation between the patient image 1 and the patient image 2, then the patient images 1 and 2 can be assumed to be spatially identical. As a consequence, there is a constraint on the determination of APT. In the example given, the constraint would be that the deformation described by APT1 is the same as the deformation described by APT2.

Figure 3:
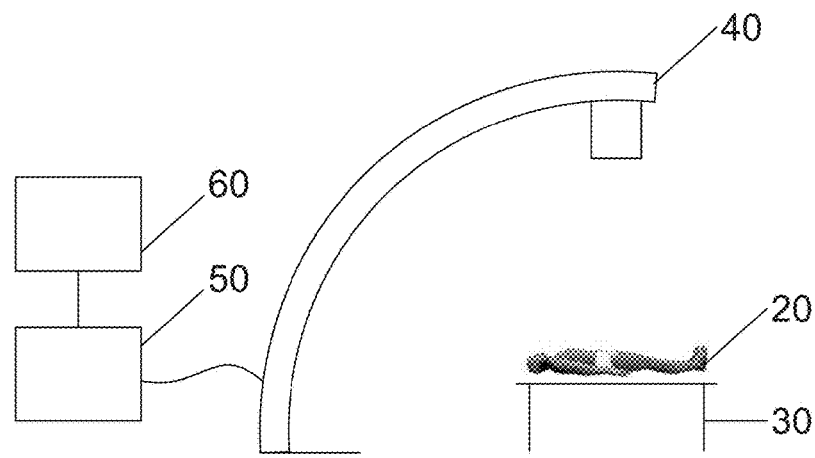
FIG. 3 shows a medical image processing system in accordance with an embodiment of the present invention.

FIG. 3 shows a medical image processing system in which a patient 20 lies on a couch 30 and an analytical device 40 is provided in order to generate an analytical image of the patient 20. The analytical device 40 is connected to a computer 50 which comprises a monitor 60. The computer 50 is used to run a program which performs the data processing method as described in this document, in order in particular to display atlas images and/or patient images and/or matched atlas images on the monitor 60.

Figure 4:
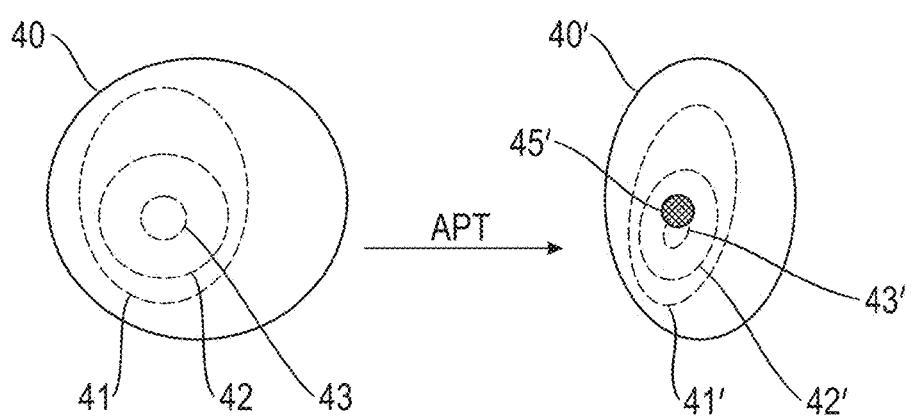
FIG. 4 illustrates how spatial meta information are matched.

FIG. 4 illustrates how spatial meta information are matched. A white atlas element 40 is shown on the left in FIG. 4, which is combined with spatial meta information on the pathological changes. The spatial meta information is represented by contour lines 41, 42 and 43 which represent lines of constant probability for a pathological change along the line if the atlas element is associated with a particular patho parameter (for instance, a particular TNM classification). For instance, the probability of a tumour inside the contour line 41 is more than 10%, the probability of a tumour inside the contour line 42 is more than 50% and the probability of a tumour inside the contour line 43 is more than 90%. The determined matching transformation is then applied to the atlas element 40 and matches the atlas element 40 to the patient element 40' which has already been segmented, for instance using the corresponding method described in this document. The matching transformation is also applied to the spatial meta information. In the example given, the matching transformation is also applied to the contour lines, resulting in the matched contour lines 41', 42' and 43', i.e. the image on the right in FIG. 4 reflects a spatial statistical probability distribution of pathological changes. This image can be overlaid with the actual image of the patient, which then for example highlights an identified pathological change in the cross-hatched area 45'. Radiotherapy can for example be planned on the basis of the combined images. Radiotherapy can for example be planned not only on the basis of the cross-hatched area 45' but also on the basis of the contour lines 41', 42' and/or 43'. It is for example possible to plan for the application of the radiotherapy treatment to be expanded to the area within the contour line 42' in order to suppress possible pathological changes which cannot yet be identified by means of analytical images. Conversely, if the total patient element 40' is usually treated, the application of the radiotherapy treatment can be restricted to the area within the contour line 41'.

It is claimed:

1. A data processing method for determining by a computer a matching transformation for matching a set of one or more images of an anatomical body structure of an associated patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the method performed by the computer comprising:

acquiring atlas data, comprising sub-steps of:
  acquiring atlas spatial information which contains spatial information on the general anatomical structure; and,
  acquiring element representation information which describes a plurality of representation data sets which contain information on representations of the plurality of atlas elements in the atlas images to be determined, wherein the element representation information describes a determination rule for determining respective representation data sets for respective atlas elements in accordance with different respective parameter sets;
acquiring patient data, comprising sub-steps of:
  acquiring the patient image set; and,
  acquiring one or more of the plurality of parameter sets which are respectively associated with the one or more images of the patient image set;
determining, on the basis of the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image; and,
determining the matching transformation which matches the atlas image set and the patient image set, by matching images associated with the same parameter set to each other,
wherein the matching transformation is operable to deform a part of the geometry of the general anatomical structure in order to match the atlas images to the patient images,
wherein a common reference system is used for a step of determining the matching transformation which step of determining comprises taking into account information on an influence on matching quality of a deformation of at least one of the atlas images associated with at least one of the parameter sets in order to determine a deformation of at least another of the atlas images which is associated with at least another of the parameter sets and includes corresponding elements which are identical to the corresponding elements included in said at least one of the atlas images.

2. The data processing method according to claim 1, wherein the determining the matching transformation comprises:
taking into account that the spatial information described by the atlas images is identical and also taking into account information on the spatial correlation between the spatial information described by the patient images in order to determine deformations described by the matching transformation which is applied in order to match the atlas images and patient images to each other.

3. The data processing method according to claim 1, wherein the matching transformation comprises a set of coupled transformations referred to as matching sub-transformations, wherein the respective matching sub-transformations respectively match the atlas images associated with one of the associated parameter sets and the patient image which is associated with the same respective associated parameter set to each other, and the matching sub-transformations are mutually coupled by each influencing a determination of the other.

4. The data processing method according to claim 1, wherein determining the atlas image set comprises:
determining the representation data sets for the corresponding elements, wherein for each atlas image to be determined, one of the representation data sets is determined for each of the corresponding elements in accordance with the determination rule, wherein the determination rule comprises an assignment rule for assigning a respective representation data set to a respective corresponding element in accordance with the parameter set associated with the patient image to which the atlas image which includes the corresponding element is to be matched; and,
determining the atlas image set comprising one or more images which are respectively associated with one of the parameter sets, by respectively using the determined representation data sets to determine the representations of the corresponding elements.

5. The data processing method according to claim 1, further comprising:
using image values of patient elements in combination with determining the matching transformation for determining the representation of one or more of the corresponding elements in the one or more atlas images.

6. The data processing method according to claim 1, wherein the determining the matching transformation, which matches one of the atlas images and one of the patient images associated with one of the parameter sets to each other, comprises determining the matching transformation on an basis of information on the matching transformation between another of the atlas images and another of the patient images associated with another of the associated parameter sets.

7. The data processing method according to claim 1, wherein:
the determination rule describes an assignment between the plurality of atlas elements and the plurality of representation data sets by describing a surjective assignment between the atlas elements and representation classes;
the respective representation classes respectively represent subsets of the plurality of representation data sets; and
for each of the respective representation classes, there is a unique set of characteristic bijective assignments between individual representation data sets of the subsets and individual parameter sets.

8. The data processing method according to claim 1, wherein the representation data sets describe at least one of the following types of information on representation:
image values for the anatomical elements;
ranges of image values for the anatomical elements;
the relationship between image values of different anatomical elements;
the relationship between image values for one or more of the anatomical elements represented in images associated with different parameter sets;
maximum image values for the anatomical elements;
minimum image values for the anatomical elements;
average image values for the anatomical elements;
standard deviations of the average image values and structures of modulations of the image values for the anatomical elements; and/or
characteristics of transitions between representations of different anatomical elements.

9. The data processing method according to claim 1, wherein:
the atlas data further comprise spatial flexibility information, the spatial flexibility information describing a flexibility of the position of atlas elements within the general anatomical structure; and
the matching transformation is determined on a basis of the spatial flexibility information.

10. The data processing method according to claim 1, further comprising:
acquiring correspondence part data which describe the corresponding elements,
wherein the acquiring the atlas data comprises acquiring coarse atlas spatial information which describes the spatial information on the general anatomical structure in less detail than the atlas spatial information used to determine the atlas image set,
wherein the acquiring the atlas data comprises applying a rigid matching transformation for matching the at least one patient image to a part of the general anatomical structure described by the coarse atlas spatial information, in order to determine the part of the general anatomical structure which allows a predetermined optimum of the matching result to be achieved, in particular a predetermined optimum of a measure of similarity, when determining the matching transformation, and wherein the corresponding elements are determined on the basis of the atlas elements included in the determined part.

11. The data processing method according to claim 1, wherein the atlas spatial information comprises a description of a plurality of different states of the general anatomical structure which are respectively described by different sets of spatial information, wherein the plurality of different states correspond in particular to a time-dependent set of spatial information which in particular comprises a description of a time-dependent vital movement of at least part of the general anatomical structure, wherein acquiring the correspondence part data comprises determining the state and in particular time, which allows a predetermined optimum of the matching result to be achieved, in particular a predetermined optimum of a measure of similarity, when determining the matching transformation.

12. The data processing method according to claim 1, further comprising:
applying the matching transformation to the atlas image set in order to determine matched atlas images or applying the matching transformation to the patient image set in order to determine matched patient images.

13. The data processing method according to claim 1 wherein:
the general anatomical structure comprises pathological changes;
the patient image is associated with one of a plurality of different parameters referred to as patho parameters, wherein the patho parameters specify the pathological changes in accordance with a classification, wherein the atlas spatial information contains a plurality of spatial information on the general anatomical structure for a plurality of patho parameters, wherein the element representation information describes a plurality of representation data sets which contain information on representations of the plurality of atlas elements in the atlas images to be determined for a plurality of patho parameters, wherein the element representation information describes a determination rule for determining respective representation data sets for respective atlas elements in accordance with different respective parameter sets and in accordance with the patho parameter associated with the set of patient images;
the acquiring the patient data comprises sub-steps of:
acquiring the patho parameter associated with the patent image; and,
wherein the acquired one or more parameter sets are respectively associated with the same patho parameter;
the determining the set of atlas images comprises:
determining, on the basis of the atlas data and the patient data, the set of atlas images which respectively represent at least a part of the general anatomical structure associated with the patho parameter by using the spatial information on the general anatomical structure associated with the patho parameter and particular representation data sets associated with the patho parameter which are determined by applying the determination rule in accordance with the patho parameter and one or more associated parameter sets and particular atlas elements acquired and referred to as corresponding elements, which are to be matched to corresponding anatomical elements represented in the patient image;
at least a part of the general anatomical structure comprises pathological changes in accordance with the patho parameter and corresponds to at least a part of the anatomical structure represented on the patient image; and
the determining the matching transformation comprises determining the matching transformation which matches the atlas image set and the patient image set, by matching images associated with the same parameter set and the same patho parameter to each other.

14. The data processing method of claim 13, wherein:
the atlas data contain spatial meta information on the pathological changes; and
the determined matching transformation matches the spatial meta information to the patient image.

15. A program embodied on a non-transitory computer readable medium, the program, when running on a computer or when loaded onto a computer, causes the computer to perform steps for determining a matching transformation for matching a set of one or more images of an anatomical body structure of an associated patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the steps when performed by the computer comprising:
acquiring atlas data, comprising sub-steps of:
acquiring atlas spatial information which contains spatial information on the general anatomical structure; and,
acquiring element representation information which describes a plurality of representation data sets which contain information on representations of the plurality of atlas elements in the atlas images to be determined, wherein the element representation information describes a determination rule for determining respective representation data sets for respective atlas elements in accordance with different respective parameter sets;
acquiring patient data, comprising sub-steps of:
acquiring the patient image set; and,
acquiring one or more of the plurality of parameter sets which are respectively associated with the one or more images of the patient image set;
determining, on the basis of the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image; and,
determining the matching transformation which matches the atlas image set and the patient image set, by matching images associated with the same parameter set to each other, and
wherein the matching transformation is designed to deform a part of the geometry of the general anatomical structure in order to match the atlas images to the patient images, and wherein a common reference system is used for a step of determining the matching transformation which step of determining comprises taking into account information on an influence on matching quality of a deformation of at least one of the atlas images associated with at least one of the parameter sets in order to determine a deformation of at least another of the atlas images which is associated with at least another of the parameter sets and includes corresponding elements which are identical to the corresponding elements included in said at least one of the atlas images.

16. A computer apparatus determining a matching transformation for matching a set of one or more images of an anatomical body structure of an associated patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the computer apparatus being configured to perform steps comprising:
acquiring atlas data, comprising sub-steps of:
acquiring atlas spatial information which contains spatial information on the general anatomical structure; and,
acquiring element representation information which describes a plurality of representation data sets which contain information on representations of the plurality of atlas elements in the atlas images to be determined, wherein the element representation information describes a determination rule for determining respective representation data sets for respective atlas elements in accordance with different respective parameter sets;
acquiring patient data, comprising sub-steps of:
acquiring the patient image set; and,
acquiring one or more of the plurality of parameter sets which are respectively associated with the one or more images of the patient image set;
determining, on the basis of the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image; and,
determining the matching transformation which matches the atlas image set and the patient image set, by matching images associated with the same parameter set to each other, and
wherein the matching transformation is designed to deform a part of the geometry of the general anatomical structure in order to match the atlas images to the patient images, and wherein a common reference system is used for a step of determining the matching transformation which step of determining comprises taking into account information on an influence on matching quality of a deformation of at least one of the atlas images associated with at least one of the parameter sets in order to determine a deformation of at least another of the atlas images which is associated with at least another of the parameter sets and includes corresponding elements which are identical to the corresponding elements included in said at least one of the atlas images.

17. A medical image processing system, comprising:
one or more analytical devices for generating patient images of an associated patient; and
the computer apparatus according to claim 16, the computer apparatus being configured to determine the matching transformation and apply the matching transformation in order to match the generated patient images and determined atlas images.

18. A non-transitory program storage medium storing a program for determining a matching transformation for matching a set of one or more images of an anatomical body structure of an associated patient, referred to as a patient image set, and a set of one or more images of a general anatomical structure, referred to as an atlas image set, wherein the general anatomical structure comprises a plurality of anatomical elements referred to as atlas elements, and each patient image is associated with one of a plurality of different parameter sets, wherein the parameter sets comprise one or more parameters which obtain when the patient images are generated, and the parameters influence representations of anatomical elements in the patient images, the program stored on the non-transitory program storage medium causing, when running on a computer or when loaded onto a computer, the computer to perform a method comprising:

acquiring atlas data, comprising sub-steps of:
acquiring atlas spatial information which contains spatial information on the general anatomical structure; and,
acquiring element representation information which describes a plurality of representation data sets which contain information on representations of the plurality of atlas elements in the atlas images to be determined, wherein the element representation information describes a determination rule for determining respective representation data sets for respective atlas elements in accordance with different respective parameter sets;

acquiring patient data, comprising sub-steps of:
acquiring the patient image set; and,
acquiring one or more of the plurality of parameter sets which are respectively associated with the one or more images of the patient image set;

determining, based on the atlas data and the patient data, the set of atlas images which respectively represent at least a part of the general anatomical structure by using the spatial information on the general anatomical structure and particular representation data sets which are determined by applying the determination rule in accordance with the one or more associated parameter sets and particular atlas elements acquired and referred to as corresponding elements, which are to be matched to corresponding anatomical elements represented in the patient image; and, determining the matching transformation which matches the atlas image set and the patient image set, by matching images associated with the same parameter set to each other, and wherein the matching transformation is designed to deform a part of the geometry of the general anatomical structure in order to match the atlas images to the patient images, and wherein determining a common reference system is used for a step of the matching transformation which step of determining comprises taking into account information on an influence on matching quality of a deformation of at least one of the atlas images associated with at least one of the parameter sets in order to determine a deformation of at least another of the atlas images which is associated with at least another of the parameter sets and includes corresponding elements which are identical to the corresponding elements included in said at least one of the atlas images.

* * * * *